United States Patent
Chodakewitz et al.

(10) Patent No.: US 6,689,761 B1
(45) Date of Patent: Feb. 10, 2004

(54) COMBINATION THERAPY FOR HIV INFECTION

(75) Inventors: Jeffrey A. Chodakewitz, Gwynedd Valley, PA (US); Emilio A. Emini, Paoli, PA (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 08/382,113

(22) Filed: Feb. 1, 1995

(51) Int. Cl.$^7$ .................... A61K 31/70; A61K 31/495
(52) U.S. Cl. .................... 514/49; 514/46; 514/50; 514/255
(58) Field of Search ............... 514/46, 49, 50, 514/255

(56) References Cited

U.S. PATENT DOCUMENTS

| | | | | |
|---|---|---|---|---|
| 4,724,232 A | * | 2/1988 | Rideout et al. | 514/50 |
| 5,028,595 A | * | 7/1991 | Soo | 514/49 |
| 5,254,539 A | * | 10/1993 | Mitsuya et al. | 514/46 |
| 5,413,999 A | * | 5/1995 | Vacca et al. | 514/231.5 |

FOREIGN PATENT DOCUMENTS

| | | | |
|---|---|---|---|
| EP | 0 494 119 | 7/1992 | |
| EP | 0 617 968 | 3/1994 | A61K/45/06 |
| WO | 9111186 | * 8/1991 | |
| WO | WO 94/26717 | 11/1994 | C07D/217/26 |
| WO | WO 91/11186 | 8/1995 | |
| WO | WO 96/00068 | 1/1996 | A61K/31/495 |

OTHER PUBLICATIONS

Vacca, et al., "L–735,524: An orally bioavailable human immunodeficiency virus type 1 . . . ", Proc. Natl. Acad. Sci., USA, vol. 91, No. 9, 4096–4100 (1994).
Database AIDSLINE, , vol. 94, No. 30, pp. 26–28 (1994).
St. Clair, et al., "In Vitro Comparison of Selected Triple–Drug Combinations . . . ", J. of Acquired Immune Deficiency Syn. and Hum. Retro., vol. 10, No. Suppl. 2, (1995), pp. S83–S91.
Mascolini, "A Lisbon Traviata", J. Int. Assoc. Physicians AIDS Care, vol. 1, No. 8, pp. 10–20, 22 (1995).
Database AIDSLINE, Abs. No. 96700812, No. 19, P. 3 (1995).
Viner, et al., Abs. No. PO–A25–0607, Int. Conf. AIDS, vol. 9, No. 1, p. 236 (1993).
Lambert, et al., "Synergistic Drug Interactions of an HIV–1 Protease Inhibitor . . . ", Antiviral Research, vol. 21, No. 4, pp. 327–342 (1993).

J. D. Armstrong III et al, Tetrahedron Letters, vol. 33, No. 44, pp. 6599–6602, (1992).
A. E. DeCamp et al., Tetrahedron Letters, vol. 32, No. 16, pp. 1867–1870, (1991).
M. T. Reetz et al., Tetrahedron Letters, vol. 35, No. 13, pp. 1869–1972, (1994).
M. T. Reetz et al., Tetrahedron Letters, vol. 34, No. 7, pp. 1119–1122, (1993).
M. T. Reetz, Angew. Chem. Int. Ed. Engl., vol. 30, No. 12, pp. 1531–1750, (Dec. 1991).
S. Kano et al., Tetrahedron Letters, vol. 32, No. 2, pp. 233–236, (1991).
J. Christopher McWilliams et al., et al., JACS, 118, pp. 11970–11971, (1996).
Choi, et al., "In Situ Complexation Directs the Stereochemistry of N–Glycosylation in the Synthesis . . . ", J. Am. Chem. Soc., 113, pp. 9377–9379 (1991).
Chu, et al., "Enantiomeric Synthesis of (+)–BCH–189 [(+)–(2S,5R)–1–[2–(Hydroxymethyl)–1, 3–oxathiolan–5–ul]. . . ", J. Org. Chem., pp. 6503–6505 (1991).
Furman, et al., "The Anti–Hepatitis B Virus Activities, Cytotoxiities, and Anabolic Profiles of the (−) and (−30 ) Enantiomers . . . ", Antimicro. Agents and Chemo., pp. 2686–2692, Dec. 1992.
Hoong, et al., "Enzyme–Mediated Enantioselective Preparation of Pure Enantiomers of the Antiviral Agent 2',3'. . . ", J. Org. Chem., 57, pp. 5563–5565 (1992).
Schinazi, et al., "Activities of the Four Optical Isomers of 2',3'–Dideoxy–3'– Thiacytidine (BCH–189) . . . ", Antimicro. Agents and Chemo., vol. 36, No. 3., pp. 672–676, Mar. 1992.

* cited by examiner

*Primary Examiner*—Russell Travers
(74) *Attorney, Agent, or Firm*—Kenneth R. Walton; Valerie J. Camara; Jack L. Tribble

(57) ABSTRACT

The combination of the HIV protease inhibitor Compound J, 3TC, and, optionally AZT, ddI, or ddC, is useful in the inhibition of HIV protease, the inhibition of HIV reverse transcriptase, the prevention or treatment of infection by HIV and the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

9 Claims, No Drawings

COMBINATION THERAPY FOR HIV INFECTION

FIELD OF THE INVENTION

The combination in this invention is useful in the inhibition of HIV protease, the inhibition of HIV reverse transcriptase, the treatment of infection by HIV and in the treatment of AIDS and/or ARC (i.e., AIDS related complex), either as compounds, pharmaceutically acceptable salts or esters (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988), demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

Nucleotide sequencing of HIV shows the presence of a pol gene in one open reading frame [Ratner, L. et al., *Nature*, 313, 277 (1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et al., *Science*, 231, 1567 (1986); Pearl, L. H. et al., *Nature*, 329, 351 (1987)].

The compound disclosed and referred to as "Compound J" in EPO 541,168, which published on May 12, 1993, is a potent inhibitor of HIV protease and is useful in the prevention of infection by HIV, the treatment of infection by HIV and the treatment of AIDS or ARC, without significant side effects or toxicity:

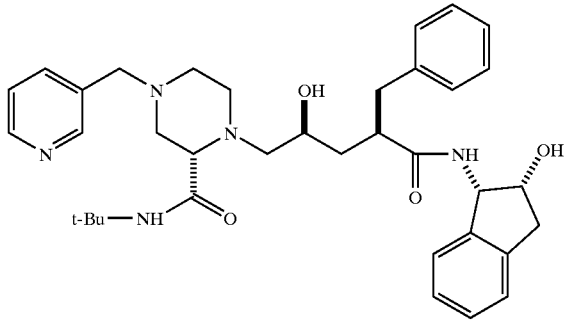

or pharmaceutically acceptable salts thereof.

Compound J

One substantial and persistent problem in the treatment of AIDS has been the ability of the HIV virus to develop resistance to the individual therapeutic agents employed to treat the disease. To solve this problem, a combination therapy for AIDS has been discovered by applicants.

Applicants demonstrate that the combination of compounds of this invention is useful in the treatment of HIV infection.

In the present invention, applicants co-administer the potent HIV protease inhibitor Compound J with the nucleoside HIV reverse transcriptase inhibitor 3TC. Optionally, a third component which is a nucleoside inhibitor of HIV reverse transcriptase, such as AZT, ddI or ddC, is added to the combination. This combination therapy is a method to enhance the effectiveness in treating AIDS and to preclude the development of resistance to the individual therapeutic agents.

SUMMARY OF THE INVENTION

The present invention involves a combination of Compound J and the nucleoside analog HIV reverse transcriptase inhibitor 3TC, and, optionally, a nucleoside inhibitor of HIV reverse transcriptase selected from AZT, ddI or ddC, or a pharmaceutically acceptable salt or ester thereof.

DETAILED DESCRIPTION OF THE INVENTION AND PREFERRED EMBODIMENTS

This invention is concerned with the combination of certain compounds, or pharmaceutically acceptable salts thereof, in the inhibition of HIV protease, the inhibition of HIV reverse transcriptase, the prevention or treatment of infection by HIV and in the treatment of the resulting acquired immune deficiency syndrome (AIDS). The combination is defined as follows:

A combination of compounds, which is Compound J and the nucleoside analog, HIV reverse transcriptase inhibitor 3TC, and, optionally a nucleoside inhibitor of HIV reverse transcriptase selected from AZT, ddI and ARC, or pharmaceutically acceptable salt or ester thereof.

One preferred combination involves the combination of Compound J and 3TC and AZT, administered simultaneously.

Another preferred combination involves the combination of Compound J, 3TC and AZT, administered alternatively.

Another preferred combination is compound J and the nucleoside inhibitor of HIV reverse transcriptase 3TC, or pharmaceutically acceptable salts thereof.

The HIV protease inhibitor Compound J is synthesized by the protocol of EP 0 541 168, published May 12, 1993. Compound J is N-(2(R)-hydroxy-1(S)-indanyl)-2(R)-phenylmethyl-4-(S)-hydroxy-5-(1-(4-(3-pyridylmethyl)-2(S)-N'-(t-butyl-carboxamido)-piperazinyl))-pentanemide, or pharmaceutically acceptable salt thereof.

The nucleoside analog 3TC has the structure

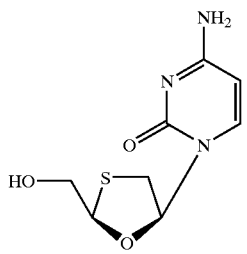

It is synthesized by the methods of C. K. Chu et al., *J. Org. Chem.* 56, 6503 (1991); W. B. Choi et al., *J. Am., Chem. Soc.* 113, 9377 (1991); L. Houng et al., *J. Org. Chem.* 57, 5563 (1992); R. F. Schinazi et al., *Antimicrob. Agents Chemother.* 36, 672 (1992); P. A. Furman et al., *Antimicrob. Agents Chemother.* 36, 2686 (1992), EP 0494119 and WO 91/11186.

The pharmaceutically acceptable salts of the present invention (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quatemized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

The pharmaceutically acceptable salts of the combination of the instant invention include the combination wherein one of the individual components is in the form of a pharmaceutically acceptable salt, or the combination wherein all of the individual components are in the form of pharmaceutically acceptable salts, or a pharmaceutically acceptable salt of the combined components (i.e., a salt of the combination). In one embodiment of the present invention, the sulfate salt of the combination is utilized.

The pharmaceutically acceptable esters in the present invention refer to non-toxic esters, preferably the alkyl esters such as methyl, ethyl, propyl, isopropyl, butyl, isobutyl or pentyl esters, of which the methyl ester is preferred. However, other esters such as phenyl-$C_{1-5}$ alkyl may be employed if desired.

Esterification of alcohols, such as Compound J of the present invention, is performed by a variety of conventional procedures, including reacting the alcohol group with the appropriate anhydride, carboxylic acid or acid chloride. These reactions, as well as other methods of esterification of alcohols, are readily apparent to the skilled artisan.

Reaction of the alcohol with the appropriate anhydride is carried out in the presence of an acylation catalyst, such as 4-DMAP (4-dimethylaminopyridine, also known as N,N-dimethylaminopyridine), pyridine, or 1,8-bis[dimethylamino]napthalene.

Reaction of the alcohol with the appropriate carboxylic acid is carried out in the presence of a dehydrating agent and, optionally, an acylation catalyst. The dehydrating agent, which serves to drive the reaction by the removal of water is selected from dicyclohexylcarbo-diimide (DCC), 1-[3-dimethylaminopropyl]-3-ethylcarbodiimide (EDC) or other water soluble dehydrating agents.

Alternatively, reaction of the alcohol with appropriate carboxylic acid can also result in esterification, if performed instead in the presence of trifluoroacetic anhydride, and, optionally, pyridine. A further variant is reacting the alcohol with appropriate carboxylic acid in the presence of N,N-carbonyldiimidazole with pyridine.

Reaction of the alcohol with the acid chloride is carried out with an acylation catalyst, such as 4-DMAP or pyridine.

Selective esterification of Compound J is performed by a variety of methods known to the skilled artisan. In one method, the alcohol is first esterified with a trichloroethyl derivative (e.g., mono-trichloroethyl succinate). After chromatographic isolation of the preferred ester, reductive elimination of the tricholoroethyl group is carried out by reaction with zinc dust in acetic acid. Alternatively, another method of selective esterification is the hydrolysis of the bis-ester.

The combination of compounds of the present invention is useful in the inhibition of HIV protease, the inhibition of HIV reverse transcriptase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC, both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

For these purposes, the combinations of the present invention may be administered orally, parenterally (including subcutaneous injections, intravenous, intramuscular, intrastemal injection or infusion techniques), by inhalation spray, or rectally, in dosage unit formulations containing conventional non-toxic pharmaceutically acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of each compound in the combination of the present invention.

These pharmaceutical compositions may be in the form of orally-administrable suspensions or tablets; nasal sprays; sterile injectable preparations, for example, as sterile injectable aqueous or oleaginous suspensions or suppositories.

In accordance with the method of the present invention, the individual components of the combination can be administered separately at different times during the course of therapy or concurrently in divided or single combination forms. For example, in a two-component combination which is the HIV protease inhibitor, Compound J, and the nucleoside HIV reverse transcriptase 3TC, treatment with 3TC can commence prior to, subsequent to or concurrent with commencement of treatment with Compound J. The instant invention is therefore to be understood as embracing all such regimes of simultaneous or alternating treatment and the term "administering" is to be interpreted accordingly.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

The compounds of this invention can be administered to humans in the dosage ranges specific for each compound. Compound J, or a pharmaceutically acceptable salt thereof, is administered orally in a dosage range between about 40 mg and about 4000 mg per day, divided into between one and four doses per day. One preferred dosage range for Compound J is between about 300 mg and about 1200 mg every 8 hours. One preferred dosage range of AZT (zidovudine) is between about 50 mg and about 600 mg every 8 hours. One preferred dosage range of 3TC is between about 20 mg and about 500 mg twice daily. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The combination of the present invention can also be combined with an optional third antiviral component which is a nucleoside inhibitor of HIV reverse transcriptase. For example, the combination of this invention may be effectively administered, whether at periods of pre-exposure and/or past exposure, in combination with effective amounts of the AIDS antivirals AZT, ddI or ddC, known to those of ordinary skill in the art.

TABLE 1

Antivirals

| Drug Name | Manufacturer | Indication |
| --- | --- | --- |
| ddI Dideoxyinosine | Bristol-Myers (New York, NY) | AIDS, ARC |
| ddC Dideoxycytidine | Hoffman-LaRoche (Nutley, NJ) | AIDS, ARC |
| Zidovudine, AZT | Burroughs-Wellcome (Research Triangle Park) | AIDS, adv, ARC, pediatric AIDS, Kaposi's sarcoma, asymptomatic HIV infection, less severe HIV disease, neurological involvement, in combination with other therapies |

AZT is synthesized by the methods of J. P. Horwitz et al., *J. Org. Chem.*, 29, 2076 (1964); R. P. Glinski et al., *J. Org. Chem.*, 38, 4299 (1973); and C. K. Chu et al., *Tetrahedron Letters*, 29, 5349 (1988). Application of AZT as a therapeutic drug in the treatment of AIDS is disclosed in U.S. Pat. No. 4,724,232.

The compound ddC is synthesized by the methods of J. P. Horwitz et al., *J. Org. Chem.*, 32, 817 (1967); R. Marumoto and M. Honjo, *Chem. Pharm. Bull.*, 22, 128 (1974); and T-S. Lin et al., *J. Med. Chem.*, 30, 440 (1987). Application of ddC as a therapeutic drug in the treatment of AIDS is disclosed in U.S. Pat. Nos. 4,979,277 and 5,028,595.

The compound ddI is synthesized by the methods of U.S. Pat. No. 5,011,774; and V. Bhat et al., *Synthetic Commun.*, 22(10), 1481–86 (1992). Application of ddI as a therapeutic drug in the treatment of AIDS is disclosed in U.S. Pat. No. 5,254,539.

Preferred combinations are simultaneous or alternating treatments of an inhibitor of HIV protease and a non-nucleoside inhibitor of HIV reverse transcriptase. An optional third component in the instant combination is a nucleoside inhibitor of HIV reverse transcriptase, such as AZT, ddC or ddI. These combinations may have synergistic effects on limiting the spread of HIV. Thus, the present invention includes triple combinations of the HIV protease inhibitor Compound J, with the nucleoside HIV reverse transcriptase inhibitor 3TC and a nucleoside HIV reverse transcriptase inhibitor selected from AZT, ddI or ddC. For such triple combinations, treatments may be simultaneous, alternating or both simultaneous and alternating.

EXAMPLE 1

Protocol for the Combination Therapy of Compound J. AZT and 3TC

In one sample, approximately 90 HIV-1 seropositive male or female adults 18 years of age or older are treated. The patients may have previous treatment with zidovudine for more than or equal to about six months. Their CD4 counts are between about 50 and 400 cells/mm$^3$ and serum viral RNA levels of more than or equal to about 20,000 copies/mL. The primary objective to the protocol is to administer Compound J at 800 mg q8h in combination with zidovudine 200 mg q8h and 3TC 150 mg twice daily.

DOSAGE/DOSAGE FORM, ROUTE, AND DOSE REGIMEN

| Group | N  | Treatment [Dose] | | |
|-------|----|------------------|---|---|
| 1 | 30 | J [800 mg q8h] | AZT [200 mg q8h] | 3TC [150 mg b.i.d] |
| 2 | 30 | Placebo to J | AZT [200 mg q8h] | 3TC [150 mg b.i.d.] |
| 3 | 30 | J [800 mg q8h] | Placebo to AZT | Placebo to 3TC |

EXAMPLE 2

Protocol for the Combination Therapy of Compound J and 3TC

In one sample, approximately 90 HIV-1 seropositive male or female adults 18 years of age or older are treated. The patients may have previous treatment with zidovudine for more than or equal to about six months. Their CD4 counts are between about 50 and 400 cells/mm$^3$ and serum viral RNA levels of more than or equal to about 20,000 copies/mL. The primary objective to the protocol is to administer Compound J at 800 mg q8h in combination with 3TC 150 mg twice daily.

DOSAGE/DOSAGE FORM, ROUTE, AND DOSE REGIMEN

| Group | N  | Treatment [Dose] | |
|-------|----|------------------|---|
| 1 | 30 | J [800 mg q8h] | 3TC [150 mg b.i.d] |
| 2 | 30 | Placebo to J | 3TC [150 mg b.i.d.] |
| 3 | 30 | J [800 mg q8h] | Placebo to 3TC |

While the foregoing specification teaches the principles of the present invention, with examples provided for the purpose of illustration, it will be understood that the practice of the invention encompasses all of the usual variations, adaptions, or modifications, as come within the scope of the following claims and its equivalents.

What is claimed is:

1. A combination of compounds, which is Compound J, nucleoside analog HIV reverse transcriptase inhibitor 3TC, and nucleoside HIV reverse transcriptase inhibitor AZT, or a pharmaceutically acceptable salt or ester thereof.

2. The method of claim 1, wherein the combination is administered simultaneously.

3. The method of claim 1, wherein the combination is administered alternatively.

4. A method of inhibiting HIV protease, comprising administering to a suitable mammal in need of such treatment an effective amount of the combination of claim 1.

5. A method of inhibiting HIV reverse transcriptase, comprising administering to a suitable mammal in need of such treatment an effective amount of the combination of claim 1.

6. A method of treating infection by HIV, AIDS or ARC, comprising administering to a suitable mammal in need of such treatment an effective amount of the combination of claim 1.

7. A pharmaceutical composition useful for inhibiting HIV protease, comprising an effective amount of the combination of claim 1, and a pharmaceutically acceptable carrier.

8. A pharmaceutical composition useful for inhibiting HIV reverse transcriptase, comprising an effective amount of the combination of claim 1, and a pharmaceutically acceptable carrier.

9. A pharmaceutical composition useful for treating infection of HIV, or for treating AIDS or ARC, comprising an effective amount of the combination of claim 1, and a pharmaceutically acceptable carrier.

\* \* \* \* \*

UNITED STATES PATENT AND TRADEMARK OFFICE
CERTIFICATE OF CORRECTION

PATENT NO. : 6,689,761 B1
DATED : February 10, 2004
INVENTOR(S) : Jeffrey A. Chodakewitz and Emilio A. Emini It is certified that error appears in the above-identified patent and that said Letters Patent is hereby corrected as shown below:

<u>Column 8,</u>
Line 8, after "which is", insert -- a therapeutically effective amount of each of --.
Lines 12, 14 and 37, after "claim", delete "1" and insert therefor -- 6 --.
Line 23, after "HIV," insert -- or of treating --.

Signed and Sealed this

Sixth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,689,761 B1  
DATED : February 10, 2004  
INVENTOR(S) : Jeffrey A. Chodakewitz et al.

Page 1 of 1

It is certified that error appears in the above-identified patent and that said Letters Patent is hereby corrected as shown below:

<u>Column 8,</u>
Line 37, claim dependency "1" (as deleted by Certificate of Correction issued April 6, 2004) should be reinstated; delete "1," and insert -- 1 --.

Signed and Sealed this

Fifth Day of October, 2004

JON W. DUDAS
*Director of the United States Patent and Trademark Office*